United States Patent [19]

Bentley et al.

[11] 4,115,646

[45] Sep. 19, 1978

[54] PROCESS FOR PREPARING 7-AMINOCEPHALOSPORANIC ACID DERIVATIVES

[75] Inventors: Peter Hubert Bentley, Rudgwick; Gerald Brooks, Reigate, both of England

[73] Assignee: Beecham Group Limited, Brentford, England

[21] Appl. No.: 826,371

[22] Filed: Aug. 22, 1977

Related U.S. Application Data

[63] Continuation of Ser. No. 652,527, Jan. 26, 1976, abandoned.

[30] Foreign Application Priority Data

Feb. 22, 1975 [GB] United Kingdom .............. 7546/75

[51] Int. Cl.² ............................................ C07D 501/36
[52] U.S. Cl. ...................................... 544/27; 544/30; 544/26
[58] Field of Search .......................... 544/30, 26, 27

[56] References Cited

U.S. PATENT DOCUMENTS 3,919,196  11/1975  Ferres et al. .................. 260/243 C Primary Examiner—Nicholas S. Rizzo
Attorney, Agent, or Firm—Jacobs & Jacobs

[57] ABSTRACT

The use of an iodolactone as an esterifying derivative in the preparation of lactonyl esters of cephalosporins substantially reduces double bond migration during the esterification reaction.

8 Claims, No Drawings

PROCESS FOR PREPARING 7-AMINOCEPHALOSPORANIC ACID DERIVATIVES

Cross Reference

This is a continuation of Ser. No. 652,527, filed Jan. 26, 1976, now abandoned.

This invention relates to an improved process for the preparation of certain esters of 7-aminocephalosporanic acid and derivatives. Our British patent specification No. 1,377,817 discloses, inter alia a process for the preparation of a class of compounds of formula (I):

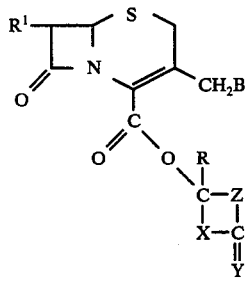

wherein
X and Y are the same or different and each represents oxygen or sulphur;
Z represents the residue of a lactone, thiolactone or dithiolactone ring system;
R represents hydrogen or an alkyl, alkenyl, alkynyl, aryl or aralkyl group, or a functional substituent;
B represents hydrogen, an acetoxy group or a pyridinium group; and
$R^1$ is an organic acylamino group, a group of formula (II):

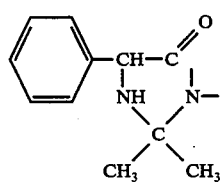

or a group of formula (III):

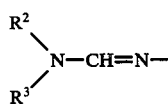

wherein $R^2$ and $R^3$ each represent a lower alkyl group, or $R^2$ and $R^3$ taken together with the nitrogen to which they are attached form a monocyclic ring;
which process comprises reacting a compound of formula (IV):

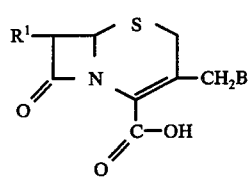

or a reactive esterifying derivative thereof, with a compound of formula (V):

or a reactive esterifying derivative thereof.

Although such a process, being a conventional esterification process, is simple and efficient, it does suffer from the disadvantage that migration of the double bond occurs during the reaction to a marked extent to produce a proportion of antibacterially inactive 2-cephem. Reactive esterifying derivatives of the compound (V) which are known from other cephalosporin esterification procedures to reduce this migration to a minimum include diazo derivatives and the reactive intermediate formed on reaction in situ with a carbodiimide. However, neither of these procedures may be satisfactorily applied to the case of the particular class of esters described above.

We have now found that the double bond migration during the esterification process can be substantially reduced by employing, as the reactive esterifying derivative of the compound (V), the corresponding iodide.

Accordingly, the present invention provides a process for the preparation of a compound of formula (IA), wherein X, Y, Z and R are as defined with respect to formula (I) above,

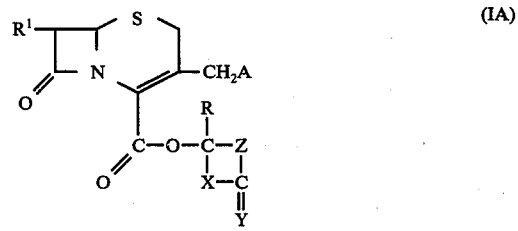

A is hydrogen, acetoxy, a carbon, nitrogen or sulphur nucleophile, or carbamoyloxy, and $R^1$ is an amino group or a group as defined with respect to formula I, which process comprises reacting a compound of formula (IV) or a reactive esterifying derivative thereof with a compound of formula (VA).

wherein R, X, Y and Z are as defined with respect to formula (I) above.

Suitable examples of the groups R, X, Y and Z are disclosed in British Specification No. 1,377,817.

The group A may be inter alia a strong carbon, nitrogen or sulphur nucleophile. Such nucleophiles displace the acetoxy group from the nucleus of 7-aminocephalosporanic acid and such displacement has been observed with various pyridines (Hale et. al. Biochem. J. 79, 403, (1961) and Spencer et. al., J. Org. Chem. (USA) 32 500, (1967)); other aromatic heterocycles (Hale et. al., loc. cit.;) Kariyone et al. J. Antibiotics, 23, 131

(1970); and Spencer et. al. loc. cit.); Xanthates and dithiocarbamates Van Heyningen et. al. J. Chem. Soc. (London) 5015 (1965)) and anilines (Bradshaw et. al. J. Chem. Soc. (London) 801 (1968)).

The group A may advantageously be a group of formula

—S—Het;

wherein 'Het' is a five of six membered heterocyclic ring containing from one to four atoms selected from N, O and S unsubstituted or substituted with one or two groups selected from lower alkyl, lower alkenyl, lower alkoxy, hydroxyalkyl, alkoxyalkyl, carboxyalkyl, trifluoromethyl, hydroxy, or halogen.

Examples of the group 'Het' include unsubstituted and substituted 1,2,3-triazolyl, 1,2,4-triazolyl, 1,2,3,4-tetrazolyl, oxazolyl, thiazolyl, 1,3,4-oxadiazolyl, 1,3,4-thiadiazolyl or 1,2,4-thiadiazolyl.

Preferably A is 2-methyl-1,3,4-thiadiazolyl-5-thio, 1-methyl-(1H)-1,2,3,4-tetrazolyl-5-thio, 2-methyl-1,3,4-oxadiazolyl-5-thio or (1H)-1,3,4-triazolyl-5-thio.

The group $R^1$ in formula (1A) has been defined as an organic acylamino group. The vast majority of antimicrobially active ceph-3-ems which have been reported to date in the literature carry a 7-acylamino group. It has been found over the years that by varying the identity of the 7-acylamino group, the spectrum and/or level of antibacterial activity of any given ceph-3-em can be modified. Similarly, in the present case a very large number of 7-acylamino groups can be introduced producing a range of compounds of widely differing spectra and levels of activity. In general, however, whatever the identity of the acylamino group $R^1$, the compounds of formula (1A) possess some activity and those who are familiar with the cephalosporin art will be aware of the range of acyl groups $R^1$ which may be introduced.

In general, therefore, $R^1$ in formula (1A) may be any of the organic acylamino groups which are present in the reported natural and semi-synthetic penicillins and cephalosporins.

Examples include acyl groups of the following general formulae (i), (ii) and (iii):

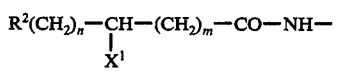

wherein $R^2$ represents hydrogen or an alkyl, cycloalkyl (especially $C_3$ to $C_6$ cycloalkyl), cycloalkenyl (especially cyclohexenyl or cyclohexadienyl), aryl (especially phenyl or substituted phenyl e.g. p-hydroxy-phenyl), heterocyclic (e.g. thienyl, pyridyl, substituted isoxazolyl such as 3-O-chlorophenyl-5-methyl isoxazol-4-yl, sydnonyl, tetrazolyl); —CH(NH₂)CO₂H; $X^1$ represents hydrogen, a hydroxyl group, a halogen atom (especially chlorine), a carboxylic acid group or carboxylic acid ester group (e.g. a phenyl or indanyl ester), an azido group, an amino group or substituted amino group (including ureido, substituted ureido, guanidino and substituted guanidino groups), a triazolyl group, a tetrazolyl group, a cyano group, an acyloxy group (e.g. formyloxy or lower alkanoyloxy group) or an esterified hydroxy group; and n and m each separately represent 0, 1, 2 or 3.

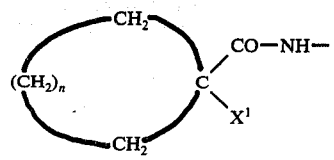

wherein n is an integer from 1 to 4 and $X^1$ is as defined in (i) above.

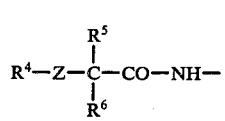

wherein $R^4$ is an alkyl, aralkyl, aryl (especially phenyl or substituted phenyl group), cycloalkyl (especially a $C_3$ to $C_6$ cycloalkyl or substituted cycloalkyl group), cycloalkenyl (especially a cyclohexenyl or cyclohexadienyl group) or a heterocyclic group (especially a thienyl or pyridyl group); $R^5$ and $R^6$ are each hydrogen lower alkyl, phenyl, benzyl or phenylethyl groups; and Z is oxygen or sulphur.

Specific examples of organic acylamino groups $R^1$ which may be present in the compounds prepared by the process of this invention include 2-thienylacetamido, phenylacetamido, 2-hydroxyphenylacetamido, 2-aminophenylacetamido, 4-pyridylacetamido, 2-amino-p-hydroxyphenylacetamido and 1-tetrazolylacetamido and w-aminoadipamido.

By the term "reactive esterifying derivative" in relation to compounds (IV) above, we mean derivatives of (IV) which when reacted with the iodo compound (V A) take part in a reaction with the consequent formation of an ester linkage:

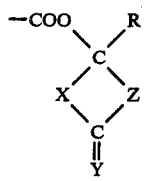

Many methods of esterification using several different reactive esterifying derivatives are known from the literature. For example, the esterification reaction defined above may be achieved by reacting a compound (V A) with a compound of formula (IV A):

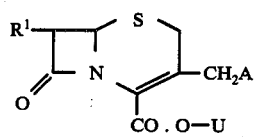

wherein $R^1$ and A are as defined with reference to formula (1A) above under conditions which cause the elimination of the elements of compound UI with the consequent formation of the ester of formula (1A). Thus, for example, U may represent hydrogen or a salt-forming ion such as sodium or potassium, or a trialkyl ammonium ion, particularly triethylammonium.

When the group $R^1$ in compound (IV) contains a free amino group, or when $R^1$ is itself amino, it is preferable that the amino group should be protected prior to the esterification reaction.

Examples of protected amino groups include the protonated amino group ($NH_3^+$) which after the acylation reaction can be converted to a free amino group by simple neutralisation; the benzyloxycarbonylamino group or substituted benzyloxycarbonylamino groups which are subsequently converted to $NH_2$ by catalytic hydrogenation; and various groups which after the acylation reaction regenerate the amino group on mild acid hydrolysis. (Alkaline hydrolysis is not generally useful since hydrolysis of the ester group takes place under alkaline conditions.)

Examples of a protected amino group which may subsequently be converted to $NH_2$ by mild acid hydrolysis include enamine groups of general formula (VI) or tautomeric modifications thereof, and α-hydroxyarylidene groups of general formula (VII) or tautomeric modifications thereof:

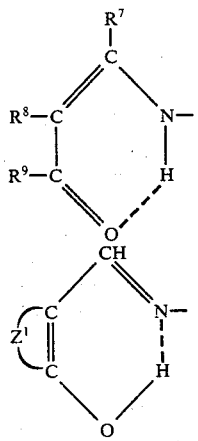

In structures (VI) and (VIII) the dotted lines represent hydrogen bonds. In structure (VI) $R^7$ is a lower alkyl group, $R^8$ is either a hydrogen atom or together with $R^7$ completes a carbocyclic ring, and $R^9$ is a lower alkyl, aryl, or lower alkoxy group. In structure (VII) $Z^1$ represents the residue of a substituted or unsubstituted benzene or naphthalene ring.

An example of a "protected amino" which can be converted to $NH_2$ after the esterification reaction is the azido group. In this case, the final conversion into $NH_2$ may be brought about by either catalytic hydrogenation or electrolytic reduction.

The advantage of the process of this invention is that double bonded migration during the reaction is minimised. It is likely that the speed of the reaction is an important factor in this reduced isomerisation, which may be caused by the carboxylate of starting material.

The speed of the process also allows a convenient synthesis of the compounds of formula (I) wherein $R^1$ is amino, which are often difficult to prepare by previously known methods.

The following examples illustrate the process of the invention In these examples, the following abbreviations are used:
Cephalothin:2-thienylacetamidocephalosporanic acid
BOC:t-Butyloxycarbonyl
DMSO:Dimethylsulphoxide
Cephaloglycin:D-α-aminophenylacetamidocephalosporanic acid
ACA:7-aminocephalosporanic acid

EXAMPLE 1

Phthalidyl 2-thienylacetamidocephalosporanate

Iodophthalide was prepared immediately prior to use by mixing acetonitrile solutions of sodium iodide (1.5mmole) and bromophthalide (1.5mmole) and stirring for 3 minutes. This solution was filtered (to remove precipitated sodium bromide) into an ice cooled DMSO solution of cephalothin (1mmole), stirred 10 minutes and poured into ice water to precipitate the required ester. Yield of crude, neutral product after work up — 90%. TLC and NMR indicate >90% ceph-3-em ester. δ ($CDCl_3$/trace DMSO) = 2.08 (d, 3H, —$OCOCH_3$), 3.61 (broad s, 2H, C2—H), 3.88 (s, 2H, α-$CH_2$), 4.6 - 5.4 (ABq + d, 3H, —$CH_2O$— + C6), 5.6 - 6.0 (m, 1H, $C_7$) 6.9 - 7.4 (d, + t, 3H, thienyl aromatics), 7.5 - 8.2 (m, ca. 5H, phthalidyl aromatics and —O$CHO$—), 8.2 - 8.6 (2d, 1H, amide N-H). $\nu_{max}$ ($CHCl_3$) 3370, 2960, 1793, 1743, 1682, 1505, 1230, 982cm$^{-1}$; λmax (EtOH) 275nm (ε, 7000)

EXAMPLE 2

Phthalidyl N-t-Butyloxycarbonylcephaloglycinate

N-t-BOC cephaloglycin (1.1mmole) in DMSO was treated with $Et_3N$ (1mmole) at room temperature and a solution of iodophthalide (1.5mmole) in acetonitrile was filtered into this. The mixture was stirred 15 minutes at room temperature and poured into ice water to precipitate the phthalidyl ester. Yield 77%. tlc and NMR indicate >90% pure ceph-3-em ester. δ ($CDCl_3$) 1.40 (s, 9H, Bu—H), 2.10 (d, 3H, —$OCOCH_3$), 3.48 (broad s, 2H, C2—H), 4.6 - 5.6 (m, 4H, C6 + —$CH_2O$— + $C_α$), 5.7 - 6.1 (m, 2H, C7 + N$H$BOC), 7.2 - 8.2 (m, 11H, αphenyl + phthalidyl aromatics and —O$CHO$— + amido NH). $\nu_{max}$($CHCl_3$), 3400, 2960, 1792, 1693, 1495, 1230, 981cm$^{-1}$; λmax (EtOH) 270nm (ε, 7400).

EXAMPLE 3

Phthalidyl 7-aminocephalosporanate (a) Sodium 7-N-(3-methoxycarbonyl-prop-2-en-2-yl)-aminocephalosporanate ACA (3.68mmole) was suspended in dry methanol and a solution of sodium (3.68mmole) in dry methanol added dropwise. On completion of the addition, methyl acetoacetate (4mmole) was added and the solution stirred 5 hours with molecular sieve (4A), filtered and evaporated. Residue was ether washed. Yield 69%. δ (DMSO) 2.03 (s, 6H, $CH_3$—C=CH + —$OCOCH_3$) 3.56 (bs, 5H, —$COOCH_3$ + C2 — H), 4.67 (s, 1H, α=•CH—), 4.7 - 5.3 (m, 3H, —O$CH_2O$— + C6), 5.5 - 5.9 (m, 1H, C7, 9.00 (d, 1H, N$H$), $\nu_{max}$ (nujol) 1762, 1665, 1620, 1280cm$^{-1}$.

(b) Phthalidyl 7-N-(3-methoxycarbonylprop-2-en-2-yl)amino cephalosporanate

The above sodium salt was esterified by the same method as Example 1 using DMSO/acetonitrile solvent at 0°-5° C. Yield 83% of pure ceph-3-em ester. δ ($CDCl_3$) 2.05 (s, 3H, —$OCOCH_3$). 3.2 - 4.0 (s at 3.68 + m, 5H, O$CH_3$ + C2—), 4.6 - 5.8 (m, 5H>C=CH— + C6 + C7 + —$CH_2O$—), 7.4 - 8.2 (m ca 5H, phthalidyl aromatics and —O$CHO$—), 9.30 (d, 1H, N$H$). $\nu_{max}$ ($CHCl_3$), 3540, 3020, 1800, 1750, 1667, 1630, 1230, 995cm$^{-1}$; λmax (EtOH) 279nm (ε, 14800). The above crude product was deprotected (HCl/acetone) to form ACA phthalidyl ester in 70% yield. Impurities in the N-protected compound were washed out after deprotection.

EXAMPLE 4

(a) Sodium 7-N-(3-methoxycarbonylprop-2-en-2-yl)-amino-3 (1-methyl-tetrazol-5'-yl-thiomethyl)-ceph-3-em-4-carboxylate Prepared similarly to Example 3(a) from tetrazole ACA Yield 74%. δ (DMSO) 2.02 (s, 3H, C$\underline{H}_3$—C+CH), 3.60 (s, 3H, —COOCH$_3$), 4.00 (s, 3H, —NCH$_3$), 3.2 – 4.9 (m, 4H, C2—H + C$\underline{H}_2$S), 4.68 (s, 1H, C=C$\underline{H}$), 5.16 (d, 1H, C6, 5.4 – 5.8 (m, 1H, C7), 9.01 (d, 1H, NH), $v_{max}$ (nujol) 3300, 1757, 1650 (shoulder), 1610, 1275cm$^{-1}$.

(b) Phthalidyl 7-N-(3-methoxycarbonylprop-2-en-2-yl)amino-3 1'-methyltetrazol-5'-yl-thiomethyl)-ceph-3-em-4-carboxylate Esterification was carried out as in Example 3(b) in 57% yield of pure ceph-3-em ester. δ (CDCl$_3$) 1.98 (s, 3H, C$\underline{H}_3$—C+CH), 3.68 (s, 3H, OC$\underline{H}_3$), 4.02(d, 3H, N—C$\underline{H}_3$) 3.3 – 5.0 (m, 5H, C2—H + 3 —CH$_2$S— +>C=C$\underline{H}$—), 5.10 (d, 1H, C$_6$) 5.40 (q, 1H, C$_7$), 7.3 – 8.2 (m, 8H, phthalidyl aromatics and —OCHO— + impurity), 9.28 (d, 1H, N$\underline{H}$), $v_{max}$(CHCl$_3$) 3540, 3000, 1780, 1740, 1653, 1610, 1260, 1210, 1155, 970. λmax (EtOH) 283nm (ε, 17500). This crude product was deprotected with HCl/acetone to yield tetrazole ACA phthalidyl ester hydrochloride (52%).

EXAMPLE 5

Phthalidyl 7-(D-α-t-butyloxycarbonyl aminophenyl acetamido)-3-(1'methyl-tetrazol-5'-ylthiomethyl)-ceph-3-em-4-carboxylate Esterification of the cephalosporin triethylammonium salt was carried out similarly to example 2 in 78% yield. δ (CDCl$_3$/trace DMSO) = 1.40 (s, 9H, Bu—H), 3.59 and 3.70 (2 broad s, 2H, C$_2$—H), 3.90 and 3.96 (2s, 3H, N—CH$_3$), 4.0 – 4.7 (m, 2H, 3—SCH$_2$—), 4.87 (d, 1H, C6), 5.38 (d, 1H, Cα—H), 5.5 – 5.9 (m, 1H, C$_7$) 6.04 (d, 1H, N$\underline{H}$BOC), 7.2 – 8.0 (m, 10H, α-phenyl + phthalidyl aromatics and —OCHO—), 8.4 – 8.7 (m, 1H, amide NH). $v_{max}$(CHCl$_3$) = 3420, 3010, 1785, 1690, 1490, 1230, 1160, 977cm$^{-1}$. λ$_{max}$ (EtOH), 268nm (ε = 8,300).

EXAMPLE 6

Phthalidyl 7-(D-α-t-butyloxycarbonyl aminophenylacetamido)-3-(2'-methyl-1', 3', 4'-thiadiazol-5'-ylthiomethyl)ceph-3-em-4-carboxylate Esterification was carried out similarly to example 2 in 67.1% yield. δ (CDCl$_3$/trace DMSO) = 1.40 (s, 9H, Bu—H), 2.70 (s, 3H, 2'—CH$_3$), 3.60 and 3.67 (2 broad s, 2H, C$_2$—H), 3.9 – 4.8 (m, 2H, 3—SCH$_2$—), 4.85 (d, 1H, C$_6$) 5.40 (d, 1H, Cα), 5.5 – 5.9 (m, 1H, C$_7$), 6.04 (d, 1H, N$\underline{H}$BOC), 7.2 – 8.0 (10H, α-phenyl + phthalidyl aromatics and —OCHO—), 8.5 – 8.8 (m, 1H, amide NH). $v_{max}$ (CHCl$_3$) = 3330, 2930, 1785, 1733, 1690, 1492, 1220, 1160, 978cm$^{-1}$. λ$_{max}$(EtOH) 274nm (ε = 11300).

EXAMPLE 7

Phthalidyl 7-p-nitrobenzyloxycarbonylamino cephalosporanate

Sodium 7-p-nitrobenzyloxycarbonylamino cephalosporanate was esterified by the method of example 1 in 48% yield. δ (CDCl$_3$) = 2.07 and 2.12 (2s, 3H, COCH$_3$), 3.63 (broad, s, 2H, C$_2$—H), 4.7 – 5.5 (m, 3H, C$_6$ + CH$_2$O—), 5.30 (s, 2H,

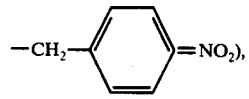

5.5 – 6.0 (m, 2H, C$_7$ + NH), 7.3 – 8.4 (m, 9H, aromatics + phthalidyl —OCHO—), $v_{max}$(CHCl$_3$), = 3400, 1785, 1740, 1520, 1350, 1230, 1050, 980cm$^{-1}$.

EXAMPLE 8

Phthalidyl N-(3-methoxycarbonylprop-2-en-2-yl)cephaloglycinate (a) Sodium N-(3-methoxycarbonylprop-2-en-2-yl)cephaloglycinate This was prepared by two methods:
(i) Analogously to example 3(a) with cephaloglycin replacing ACA. Yield 89%.
(ii) By acylation of ACA sodium salt with an activated derivative of D-α-N-(3-methoxycarbonylprop-2-en-2-yl)aminophenylacetic acid (see J. Med. Chem. 9 749, 1966). The aqueous solution was freeze dried-yield 50%.

(b) Phthalidyl N-(3-methoxycarbonylprop-2-en-2-yl)cephaloglycinate

The above sodium salt was esterified according to example 1 in 53% yield.

EXAMPLE 9

Phthalidyl 7-[D-α-N-(3'-methoxycarbonylprop-2'-en-2'-yl) aminophenylacetamido]-3-[1''-methyltetrazol-5''-ylthiomethyl]ceph-3-em-4-carboxylate Sodium 7-[D-α-N-(3'-methoxycarbonylprop-2'-en-2'-yl) aminophenylacetamido]-3-[1''-methyltetrazol-5''-ylthiomethyl]ceph-3-em-4-carboxylate was prepared and esterified as for example 8.

EXAMPLE 10

Phthalidyl 7-[D-α-N-(3'-methoxycarbonylprop-2'-en-2'-yl) aminophenylacetamido]-3-[2''-methyl-1'',3'',4''-thiadiazol-5''-ylthiomethyl]ceph-3-em-4-carboxylate Sodium 7-[D-α-N-(3'-methoxycarbonylprop-2'-en-2'-yl) aminophenylacetamido]-2-[2''-methyl-1'',3'',4''-thiadiazol-5''-ylthiomethyl]ceph-3-em-4-carboxylate was prepared and esterified as for example 8.

EXAMPLE 11

Phthalidyl 7-[N-(3'-methoxycarbonylprop-2'-en-2'-yl)amino]-3-[2''-methyl-1'',3'',4''-thiadiazol-5''-ylthiomethyl]ceph-3-em-4-carboxylate Sodium 7-[N-(3'-methoxycarbonylprop-2'-yl)amino]-3-[2''-methyl-1'',3'',4''-thiadiazol-5''-ylthiomethyl- ]ceph-2-em-4-carboxylate was prepared and esterified analogously to example 3.

EXAMPLE 12

Phthalidyl 7-[N-(3'-methoxycarbonylprop-2'-en-2'-yl)amino]-3-carbamoyloxy-methylceph-3-em-4-carboxylate Sodium 7-[N-(3'-methoxycarbonylprop-2'-yl)amino]-3-carbamoyloxy-methylceph-3-em-4-carboxylate was prepared and esterified analogously to example 3.

EXAMPLE 13

Phthalidyl 7-(p-nitrobenzyloxycarbonylamino)-3-carbamoyloxymethylceph-3-em-4-carboxylate 7-(p-nitrobenzyloxycarbonylamino)-3-carbamoyloxymethylceph-3-em-4-carboxylic acid was esterified according to example 2.

EXAMPLE 14

N-phthaloylcephalosporin C bis-phthalidyl ester

N-phthaloylcephalosporin C as the di-sodium salt (5mmole) was esterified as in example 1 using iodophthalide (from 15mmole of bromophthalide). After 10 minutes the bis phthalidyl ester (2.3g) precipitated on the addition of ice-water.

EXAMPLE 15

(a) Phthalidyl 7-D-α-t-butyloxycarbonylaminophenylacetamido-3-carbamoyloxy-methyl-3-cephem-4-carboxylate A solution of 7-D-α-t-butyloxycarbonylaminophenylacetamido-3-carbamoyloxymethyl-3-cephem-4-carboxylic acid (1.02g., 2mmole) in dimethyl sulphoxide (16 ml) is treated with triethylamine (0.28 ml., 2mmole) and a freshly prepared solution of iodophthalide (3mmole) in acetonitrile (8 mls) is added. After 15 mins. at 20° ice-water is added and the solid collected. A solution of the latter is ethyl acetate is washed with dilute sodium bicarbonate, water, dried and evaporated. Precipitation of the residue from ethyl acetate petrol ether gives the desired ester (1.5g.).

(b) Phthalidyl 7-D-α-aminophenylacetamido-3-carbamoyloxymethyl-3-cephem-4-carboxylate The foregoing crude ester (1.6g.) is treated with chilled trifluoroacetic acid (15 mls) over 40 mins. Evaporation and trituration with ether gives the title compound as its trifluoroacetate (1.5g.). This shows one major zone on biochromatography $R_f = 0.75$ in n-Butanol-ethanol-water.

We claim:
1. A process for the preparation of a compound of formula (IA):

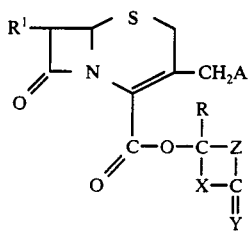

(IA)

wherein
X and Y are both oxygen;
Z is 1,2-phenylene unsubstituted or substituted by alkoxy, nitro or halogen;
R is hydrogen, phenyl or methyl;
A is hydrogen, acetoxy, carbamoyloxy or a 1,2,3-triazolyl, 1,2,4-triazolyl, 1,2,3,4-tetrazolyl, oxazolyl, thiazolyl, 1,3,4-oxadiazolyl, 1,3,4-thiadiazolyl or 1,2,4-thiadiazolyl group;
$R^1$ is an amino group, an organic acylamino group which is conventional for cephalosporin side chains, or a group of formula:

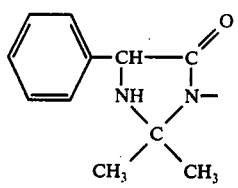

which process is characterized by esterifying a compound of formula:

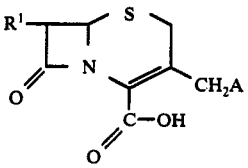

or a salt thereof, with an iodolactone of formula:

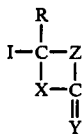

to form the corresponding 3-cephem cephalosporin lactonyl ester substantially exclusively.
2. A process according to claim 1 in which A is 2-methyl-1,3,4-thiadiazolyl-5-thio, 1-methyl-(1H)-1,2,3,4-tetrazolyl-5-thio, 2-methyl-1,3,4-oxadiazolyl-5-thio or (1H)-1,3,4-triazolyl-5-thio.
3. A process according to claim 1 in which the organic acylamino side chain is 2-thienyl-acetamido, phenylacetamido, 2-hydroxyphenylacetamido, 2-aminophenylacetamido, 4-pyridylacetamido, 2-amino-p-hydroxyphenylacetamido, 1-tetrazolylacetamido or ω-aminoadipamido.
4. A process according to claim 1 in which the esterification is carried out with reduced double bond migration.
5. In a process for the preparation of a 3-cephem cephalosporin lactonyl ester by the esterification of the unesterified 3-cephem cephalosporin having a COOH group in the 4-position, the improvement of carrying out esterification at the 4-position COOH group of the cephalosporin by reaction with an iodolactone as esterifying agent to produce the 3-cephem cephalosporin lactonyl ester substantially exclusively and reducing double bond migration during esterification with minimal formation of 2-cephem isomer, the iodolactone having the formula:

$$\begin{array}{c} R \\ | \\ I-C-Z \\ | \quad | \\ X-C \\ \parallel \\ Y \end{array}$$

wherein

R is hydrogen, phenyl or methyl;

X and Y are both oxygen; and

Z is 1,2-phenylene unsubstituted or substituted by alkoxy, nitro or halogen.

6. A process according to claim 5 where the esterifying agent is iodophthalide.

7. A process for the preparation of a compound of formula (IA):

(IA)

wherein

X and Y are both oxygen:

Z is 1,2-phenylene unsubstituted or substituted by alkoxy, nitro or halogen;

R is hydrogen, phenyl or methyl;

A is hydrogen, acetoxy, carbamoyloxy or a 1,2,3-triazolyl, 1,2,4-triazolyl, 1,2,3,4-tetrazolyl, oxazolyl, thiazolyl, 1,3,4-oxadiazolyl, 1,3,4-thiadiazolyl or 1,2,4-thiadiazolyl group;

$R^1$ is an amino group, or an amino group protected by protonation or by a benzyloxycarbonyl, p-nitrobenzyloxycarbonyl or 3-methoxycarbonyl-2-prop-2-en-2-yl group, an organic acylamino group selected from 2-thienylacetamido, phenylacetamido, 2-hydroxyphenylacetamido, 4-pyridylacetamido-, 2-amino-p-hydroxyphenyl acetamido, 1-tetrazolylacetamido and ω-aminoadipamido or a group of formula:

which process is characterized by esterifying a compound of formula:

or a sodium, potassium or triethylammonium salt thereof, wherein $R^1$ and A are as defined with reference to formula (IA), with a compound of formula:

$$\begin{array}{c} R \\ | \\ I-C-Z \\ | \quad | \\ X-C \\ \parallel \\ Y \end{array}$$

wherein R, X, Y and Z are as defined with reference to formula (IA) to form the corresponding 3-cephem cephalosporin lactonyl ester substantially exclusively.

8. A process for the preparation of a compound of formula (IA):

(IA)

wherein $R^1$ is selected from the group consisting of 2-thienylacetamido-, t-butoxycarbonylaminophthylacetamido-, 3-methoxycarbonyl-prop-2-en-2-yl, p-nitrobenzyloxycarbonyl, and ω-N-phthalidoylaminophthalidyladipamido, and A is selected from the group consisting of acetoxy, 1-methyltetrazol-5'-ylthio, 2-methyl-1,3,4-thiadiazol-5-ylthiomethyl, and carbamoyloxy, which process comprises esterifying a sodium or triethyl ammonium salt of a compound of formula:

wherein $R^1$ is ω-N-phthalidoylamino or is as defined with reference to formula (IA), and A is as defined with reference to formula (IA), with a compound of formula:

* * * * *